United States Patent [19]

Ala-Kokko et al.

[11] Patent Number: 5,045,449
[45] Date of Patent: Sep. 3, 1991

[54] METHODS OF DETECTING A GENETIC PREDISPOSITION FOR VASCULAR ANEURYSMS

[75] Inventors: Leena M. Ala-Kokko, Philadelphia, Pa.; Clinton T. Baldwin, Voorhees, N.J.; Sirpa I. Kontusaari, Philadelphia, Pa.; S. Helena Kuivaniemi, Philadelphia, Pa.; Darwin J. Prockop, Philadelphia, Pa.; Gerardus C. Tromp, Philadelphia, Pa.

[73] Assignee: Thomas Jefferson University, Philadelphia, Pa.

[21] Appl. No.: 365,848

[22] Filed: Jun. 14, 1989

[51] Int. Cl.$^5$ .................. C12Q 1/68; C07H 15/12; C12N 15/00
[52] U.S. Cl. .................................. 435/6; 536/27; 935/77; 935/78
[58] Field of Search ............... 435/6; 436/501, 525, 436/526; 536/27; 935/77, 78

[56] References Cited

U.S. PATENT DOCUMENTS 4,683,195  7/1987  Mullis et al. .......................... 435/6
4,683,202  7/1987  Mullis .................................. 435/91

OTHER PUBLICATIONS

Miskulin et al., "Human Type III Collagen Gene Expression Is Coordinately Modulated with the Type I Collagen Genes During Fibroblast Growth," Biochemistry 25, 1408–1413 (1986).
Prockop et al., New England Journal of Medicine, 311:376–386 (1984).
Prockop et al., J. Clin. Invest., 75:783–787 (1985).
Prockop, Hospital Practice, Feb. 15, 1986.
Pope et al., The Lancet, 973–975 (May 2, 1981).
Liau et al., J. Biol. Chem., 260:3773–3777 (1985).
Wood et al., Gene, 61:225–230 (1987).
Brandt et al., Biochem. J., 219:625–634 (1984).
Messing, J., Methods In Enzymology, 101:20–78 (1983).
Liodl et al., Nucleic Acids Res., 12:9383–9394.
Chu et al., J. Biol. Chem., 260:4357–4363 (1985).
Mankoo et al., Nucleic Acids Res., 16:2337 (1988).
Toman et al., Nucleic Acids Res., 16:7201 (1988).
Prockop, D., Arthritis and Rheumatism, 31:1–8 (1988).
*Harrison's Principles of Internal Medicine*, 12th Ed., "Aneurysms", p. 1016.
Suzanne Menashi et al., "Collagen in Abdominal Aortic Aneurysm: Typing, Content, and Degradation," *Journal of Vascular Surgery*, vol. 6, No. 6, pp. 578–582 (1987).

Primary Examiner—Robert A. Wax
Assistant Examiner—Mindy B. Fleisher
Attorney, Agent, or Firm—Woodcock, Washburn, Kurtz, Mackiewicz & Norris

[57] ABSTRACT

Methods of determining genetic predisposition for vascular aneurysm in mammals are disclosed. The base sequence of Type III procollagen DNA of the person tested is compared to the sequence of a standard proα1-(III) sequence. Differences in the base sequence of the test DNA indicate an increased likelihood that the person will develop vascular aneurysm. Family members of the mammal tested can also be tested to determine if they also have a genetic predisposition to vascular aneurysm by testing for the presence of the mutation in the proα1(III) gene of the family members.

4 Claims, 8 Drawing Sheets

CGGGCCCGGTGCTGAAGGGCAGGGAACAACTTGATGGTGCTACTTTGAACTGCTTTTCTTTTCTCCTTTTTGCACAAAGAG

TCTCATGTCTGATATTTAGACATGATGAGCTTTGTGCAAAAGGGGAGCTGGCTACTTCTCGCTCTGCTTCATCCCACTATT 60
MetMetSerPheValGlnLysGlySerTrpLeuLeuLeuAlaLeuLeuHisProThrIle 20

ATTTTGGCACAACAGGAAGCTGTTGAAGGAGGATGTTCCCATCTTGGTCAGTCCTATGCGGATAGAGATGTCTGGAAGCAA 141
IleLeuAlaGlnGlnGluAlaValGluGlyGlyCysSerHisLeuGlyGlnSerTyrAlaAspArgAspValTrpLysPro 47

GAACCATGCCAAATATGTGTCTGTGACTCAGGATCCGTTCTCTGCGATGACATAATATGTGACGATCAAGAATTAGACTGC 222
GluProCysGlnIleCysValCysAspSerGlySerValLeuCysAspAspIleIleCysAspAspGlnGluLeuAspCys 74

CCCAACCCAGAAATTCCATTTGGAGAATGTTGTGCAGTTTGCCCACAGCCTCCAACTGTCCCTACTCGCCCTCCTAATGGT 303
ProAsnProGluIleProPheGlyGluCysCysAlaValCysProGlnProProThrAlaProThrArgProProAsnGly 101

CAAGGACCTCAAGGCCCCAAGGGAGATCCAGGCCCTCCTGGTATTCCTGGGAGAAATGCTGACCCTGGTATTCCAGGACAA 384
GlnGlyProGlnGlyProLysGlyAspProGlyProProGlyIleProGlyArgAsnGlyAspProGlyIleProGlyGln 128

CCAGGGTCCCCTGGTTCTCCTGGCCCCCCTGGAATCTGTGAATCATGCCCTACTGGTCCTCAGAACTATTCTCCCCAGTAT 465
ProGlySerProGlySerProGlyProProGlyIleCysGluSerCysProThrGlyProGlnAsnTyrSerProGlnTyr 155

GATTCATATGATGTCAAGTCTGGAGTAGCAGTAGGAGGACTCGCAGGCTATCCTGGACCAGCTGGCCCCCCAGGCCCTCCC 546
AspSerTyrAspValLysSerGlyValAlaValGlyGlyLeuAlaGlyTyrProGlyProAlaGlyProProGlyProPro 182

GGTCCCCCTGGTACATCTGGTCATCCTGGTTCCCCTGGATCTCCAGGATACCAAGGACCCCCTGGTGAACCTGGGCAAGCT 627
GlyProProGlyThrSerGlyHisProGlySerProGlySerProGlyTyrGlnGlyProProGlyGluProGlyGlnAla 209

PRIOR ART

Fig. 1A

```
GGTCCTTCAGGCCCTCCAGGACCTCCTGGTGCTATAGGTCCATCTGGTCCTGCTGGAAAAGATGGAGAATCAGGTAGACCC  708
GlyProSerGlyProProGlyProProGlyAlaIleGlyProSerGlyProAlaGlyLysAspGlyGluSerGlyArgPro  236

GGACGACCTGGAGAGCGAGGATTGCCTGGACCTCCAGGTATCAAAGGTCCAGCTGGGATACCTGGATTCCCTGGTATGAAA  789
GlyArgProGlyGluArgGlyLeuProGlyProProGlyIleLysGlyProAlaGlyIleProGlyPheProGlyMetLys  263

GGACACAGAGGCTTCGATGGACGAAATGGAGAAAAGGGTGAAACAGGTGCTCCTGGATTAAAGGGTGAAAATGGTCTTCAA  870
GlyHisArgGlyPheAspGlyArgAsnGlyGluLysGlyGluThrGlyAlaProGlyLeuLysGlyGluAsnGlyLeuPro  290

GGCGAAAATCGAGCTCCTGGACCCATGGGTCCAAGAGGGGCTCCTGGTGAGCGAGGACGGCCAGGACTTCCTGGGGCTGCA  951
GlyGluAsnGlyAlaProGlyProMetGlyProArgGlyAlaProGlyGluArgGlyArgProGlyLeuProGlyAlaAla  317

GGTGCTCGGGGTAATGACGGTGCTCGAGGCAGTGATGGTCAACCAGGCCCTCCTGGTCCTCCTGGAACTGCCGGATTCCCT 1032
GlyAlaArgGlyAsnAspGlyAlaArgGlySerAspGlyGlnProGlyProProGlyProProGlyThrAlaGlyPhePro  344

GGATCCCCTGGTGCTAAGGGTGAAGTTGGACCTCCAGGGTCTCCTGGTTCAAATGGTGCCCCTGGACAAAGAGGAGAACCT 1113
GlySerProGlyAlaLysGlyGluValGlyProAlaGlySerProGlySerAsnGlyAlaProGlyGlnArgGlyGluPro  371

GGACCTCAGGGACACGCTGGTGCTCAAGGTCCTCCTGGCCCTCCTGGGATTAATGGTAGTCCTGGTGGTAAAGGCGAAATG 1194
GlyProGlnGlyHisAlaGlyAlaGlnGlyProProGlyProProGlyIleAsnGlySerProGlyGlyLysGlyGluMet  398
```

PRIOR ART

Fig. 1B

```
GGTCCCGCTGGCATTCCTGGAGCTCCTGGACTGATGGGAGCCCGGGGTCCTCCAGGACCAGCCGGTGCTAATGGTGCTCCT 1275
GlyProAlaGlyIleProGlyAlaProGlyLeuMetGlyAlaArgGlyProProGlyProAlaGlyAlaAsnGlyAlaPro  425

GGACTGCGAGGTGGTGCAGGTGAGCCTGGTAAGAATGGTGCCAAAGGAGAGCCCGGACCACGTGGTGAACGCGGTGAGGCT 1356
GlyLeuArgGlyGlyAlaGlyGluProGlyLysAsnGlyAlaLysGlyGluProGlyProArgGlyGluArgGlyGluAla  452

GGTATTCCAGGTGTTCCAGGAGCTAAAGGCGAAGATGGCAAGGATGGATCACCTGGAGAACCTGGTGCAAATGGGCTTCCA 1437
GlyIleProGlyValProGlyAlaLysGlyGluAspGlyLysAspGlySerProGlyGluProGlyAlaAsnGlyLeuPro  479

GGAGCTGCAGGAGAAAGGGGTGCCCCTGGGTTCCGAGGACCTGCTGGACCAAATGGCATCCCAGGAGAAAAGGGTCCTGCT 1518
GlyAlaAlaGlyGluArgGlyAlaProGlyPheArgGlyProAlaGlyProAsnGlyIleProGlyGluLysGlyProAla  506

GGAGAGCGTGGTGCTCCAGGCCCTGCAGGGCCCAGAGGAGCTGCTGGAGAACCTGGCAGAGATGGCGTCCCTGGAGGTCCA 1599
GlyGluArgGlyAlaProGlyProAlaGlyProArgGlyAlaAlaGlyGluProGlyArgAspGlyValProGlyGlyPro  533

GGAATGAGGGGCATGCCCGGAAGTCCAGGAGGACCAGGAAGTGATGGGAAACCAGGGCCTCCCGGAAGTCAAGGAGAAAGT 1680
GlyMetArgGlyMetProGlySerProGlyGlyProGlySerAspGlyLysProGlyProProGlySerGlnGlyGluSer  560

GGTCGACCAGGTCCTCCTGGGCCATCTGGTCCCCGAGGTCAGCCTGGTGTCATGGGCTTCCCCGGTCCTAAAGGAAATGAT 1761
GlyArgProGlyProProGlyProSerGlyProArgGlyGlnProGlyValMetGlyPheProGlyProLysGlyAsnAsp  587

GGTGCTCCTGGTAAGAATGGAGAACGAGGTGGCCCTGGAGGACCTGGCCCTCAGGGTCCTCCTGGAAAGAATGGTGAAACT 1842
GlyAlaProGlyLysAsnGlyGluArgGlyGlyProGlyGlyProGlyProGlnGlyProProGlyLysAsnGlyGluThr  614
```

PRIOR ART

*Fig. 1C*

GGACCTCAAGGACCCCCAGGGCCTACTGGCCCTGGTGGTGACAAAGGAGACACAGGACCCCCTGGTCCACAAGGATTACAA 1923
GlyProGlnGlyProProGlyProThrGlyProGlyGlyAspLysGlyAspThrGlyProProGlyProGlnGlyLeuGln 641

GGCTTGCCTGGTACAGGTGGTCCTCCAGGAGAAAATGGAAAACCTGGGGAACCAGGTCCAAAGGGTGATGCCGGTGCACCT 2004
GlyLeuProGlyThrGlyGlyProProGlyGluAsnGlyLysProGlyGluProGlyProLysGlyAspAlaGlyAlaPro 668

GGAGCTCCAGGAGGCAAGGGTGATGCTGGTGCCCCTGGTGAACGTGGACCTCCTGGATTGGCAGGGGCCCCAGGACTTAGA 2085
GlyAlaProGlyGlyLysGlyAspAlaGlyAlaProGlyGluArgGlyProProGlyLeuAlaGlyAlaProGlyLeuArg 695

GGTGGAGCTGGTCCCCCTGGTCCCGAAGGAGGAAAGGGTGCTGCTGGTCCTCCTGGGCCACCTGGTGCTGCTGGTACTCCT 2166
GlyGlyAlaGlyProProGlyProGluGlyGlyLysGlyAlaAlaGlyProProGlyProProGlyAlaAlaGlyThrPro 722

GGTCTGCAAGGAATGCCTGGAGAAAGAGGAGGTCTTGGAAGTCCTGGTCCAAAGGGTGACAAGGGTGAACCAGGCGGCCCA 2247
GlyLeuGlnGlyMetProGlyGluArgGlyGlyLeuGlySerProGlyProLysGlyAspLysGlyGluProGlyGlyPro 749

GGTGCTGATGGTGTCCCAGGGAAAGATGGCCCAAGGGGTCCTACTGGTCCTATTGGTCCTCCTGGCCCAGCTGGCCAGCCT 2328
GlyAlaAspGlyValProGlyLysAspGlyProArgGlyProThrGlyProIleGlyProProGlyProAlaGlyGlnPro 776

GGAGATAAGGGTGAAGGTGGTGCCCCCGGACTTCCAGGTATAGCTGGACCTCGTGGTAGCCCTGGTGAGAGAGGTGAAACT 2409
GlyAspLysGlyGluGlyGlyAlaProGlyLeuProGlyIleAlaGlyProArgGlySerProGlyGluArgGlyGluThr 803

GGCCCTCCAGGACCTGCTGGTTTCCCTGGTGCTCCTGGACAGAATGGTGAACCTGGTGGTAAAGGAGAAAGAGGGGCTCTG 2490
GlyProProGlyProAlaGlyPheProGlyAlaProGlyGlnAsnGlyGluProGlyGlyLysGlyGluArgGlyAlaPro 830

PRIOR ART

Fig. 1D

```
GGTGAGAAAGGTGAAGGAGGCCCTCCTGGAGTTGCAGGACCCCCTGGAGGTTCTGGACCTGCTGGTCCTCCTGGTCCCCAA 2571
GlyGluLysGlyGluGlyGlyProProGlyValAlaGlyProProGlyGlySerGlyProAlaGlyProProGlyProGln  857

GGTGTCAAAGGTGAACGTGGCAGTCCTGGTGGACCTGGTGCTGCTGGCTTCCCTGGTGCTCGTGGTCTTCCTGGTCCTCCT 2652
GlyValLysGlyGluArgGlySerProGlyGlyProGlyAlaAlaGlyPheProGlyAlaArgGlyLeuProGlyProPro  884

GGTAGTAATGGTAACCCAGGACCCCCAGGTCCCAGCGGTTCTCCAGGCAAGGATGGGCCCCCAGGTCCTGCGGGTAACACT 2733
GlySerAsnGlyAsnProGlyProProGlyProSerGlySerProGlyLysAspGlyProProGlyProAlaGlyAsnThr  911

GGTGCTCCTGGCAGCCCTGGAGTGTCTGGACCAAAAGGTGATGCTGGCCAACCAGGAGAGAAGGGATCGCCTGGTGCCCAG 2814
GlyAlaProGlySerProGlyValSerGlyProLysGlyAspAlaGlyGlnProGlyGluLysGlySerProGlyAlaGln  938

GGCCCACCAGGAGCTCCAGGCCCACTTGGGATTGCTGGGATCACTGGAGCACGGGGTCTTGCAGGACCACCAGGCATGCCA 2895
GlyProProGlyAlaProGlyProLeuGlyIleAlaGlyIleThrGlyAlaArgGlyLeuAlaGlyProProGlyMetPro  965

GGTCCTAGGGGAAGCCCTGGCCCTCAGGGTGTCAAGGGTGAAAGTGGAAACCAGGAGCTAACGGTCTCAGTGGAGAACGT 2976
GlyProArgGlySerProGlyProGlnGlyValLysGlyGluSerGlyLysProGlyAlaAsnGlyLeuSerGlyGluArg  992

GGTCCCCCTGGACCCCAGGGTCTTCCTGGTCTGGCTGGTACAGCTGGTGAACCTGGAAGAGATGGAAACCCTGGATCAGAT 3057
GlyProProGlyProGlnGlyLeuProGlyLeuAlaGlyThrAlaGlyGluProGlyArgAspGlyAsnProGlySerAsp 1019

GGTCTTCCAGGCCGAGATGGATCTCCTGGTGGCAAGGGTGATCGTGGTGAAAATGGCTCTCCTGGTGCCCCTGGCGCTCCT 3138
GlyLeuProGlyArgAspGlySerProGlyGlyLysGlyAspArgGlyGluAsnGlySerProGlyAlaProGlyAlaPro 1046
```

PRIOR ART

Fig. 1E

```
GGTCATCCAGGCCCACCTGGTCCTGTCGGTCCAGCTGGAAAGAGTGGTGACAGAGGAGAAAGTGGCCCTGCTGGCCCTGCT  3219
GlyHisProGlyProProGlyProValGlyProAlaGlyLysSerGlyAspArgGlyGluSerGlyProAlaGlyProAla  1073

GGTGCTCCCGGTCCTGCTGGTTCCCGAGGTGCTCCTGGTCCTCAAGGCCCACGTGGTGACAAAGGTGAAACAGGTGAACGT  3300
GlyAlaProGlyProAlaGlySerArgGlyAlaProGlyProGlnGlyProArgGlyAspLysGlyGluThrGlyGluArg  1100

GGAGCTGCTGGCATCAAAGGACATCGAGGATTCCCTGGTAATCCAGGTGCCCCAGGTTCTCCAGGCCCTGCTGGTCAGCAG  3381
GlyAlaAlaGlyIleLysGlyHisArgGlyPheProGlyAsnProGlyAlaProGlySerProGlyProAlaGlyGlnGln  1127

GGTGCAATCGGCAGTCCAGGACCTGCAGGCCCCAGAGGACCTGTTGGACCCAGTGGACCTCCTGGCAAAGATGGAACCAGT  3462
GlyAlaIleGlySerProGlyProAlaGlyProArgGlyProValGlyProSerGlyProProGlyLysAspGlyThrSer  1154

GGACATCCAGGTCCCATTGGACCACCAGGGCCTCGAGGTAACAGAGGTGAAAGAGGATCTGAGGGCTCCCCAGGCCACCCA  3543
GlyHisProGlyProIleGlyProProGlyProArgGlyAsnArgGlyGluArgGlySerGluGlySerProGlyHisPro  1181

GGGCAACCAGGCCCTCCTGGACCTCCTGGTGCCCCTGGTCCTTGC                                    3588
GlyGlnProGlyProProGlyProProGlyAlaProGlyProCys                                    1196
```

PRIOR ART

*Fig. 1F*

TAA 4401

ACC AAA CTC TAT CTG AAA TCC CAA CAA AAA AAA TTT AAC TCC ATA TGT GTT CCT CTT 4458

GTT CTA ATC TTG TCA ACC AGT GCA AGT GAC CGA CAA AAT TCC AGT TAT TTA TTT CCA 4515

AAA TGT TTG GAA ACA GTA TAA TTT GAC AAA GAA AAA TGA TAC TTC TCT TTT TTT GCT 4572

GTT CCA CCA AAT ACA ATT CAA ATG CTT TTT GTT TTA TTT TTT TAC CAA TTC CAA TTT 4629

CAA AAT GTC TCA ATG GTG CTA TAA TAA ATA AAC TTC AAC ACT CTT TAT GAT AAC AAC 4686

ACT GTG TTA TAT TCT TTG AAT CCT AGC CCA TCT GCA GAG CAA TGA CTG TGC TCA CCA 4743

GTA AAA GAT AAC CTT TCT TTC TGA AAT AGT CAA ATA CGA AAT TAG AAA AGC CCT CCC 4800

TAT TTT AAC TAC CTC AAC TGG TCA GAA ACA CAG ATT GTA TTC TAT GAG TCC CAG AAG 4857

ATG AAA AAA ATT TTA TAC GTT GAT AAA ACT TAT AAA TTT CAT TGA TTA ATC TCC TGG 4914

AAG ATT GGT TTA AAA AGA AAA GTG TAA TGC AAG AAT TTA AAG AAA TAT TTT TAA AGC 4971

PRIOR ART

Fig. 2A

CAC AAT TAT TTT AAT ATT GGA TAT CAA CTG CTT GTA AAG GTG CTC CTC TTT TTT CTT 5028
GTC ATT GCT GGT CAA GAT TAC TAA TAT TTG GGA AGG CTT TAA AGA CGC ATG TTA TGG 5085
TGC TAA TGT ACT TTC ACT TTT AAA CTC TAG ATC AGA ATT GTT GAC TTG CAT TCA GAA 5142
CAT AAA TGC ACA AAA TCT GTA CAT GTC TCC CAT CAG AAA GAT TCA TTG GCA TGC CAC 5199
AGG GAT TCT CCT CCT TCA TCC TGT AAA GGT CAA CAA TAA AAA CCA AAT TAT GGG GCT 5256
GCT TTT GTC ACA CTA GCA TAG AGA ATG TGT TGA AAT TAA ACT TTG TAA GCT TGT ATG 5313
TGG TTG TTG ATC TTT TTT TTC CTT ACA GAC ACC CAT AAT AAA ATA 5352

PRIOR ART

*Fig. 2B*

METHODS OF DETECTING A GENETIC PREDISPOSITION FOR VASCULAR ANEURYSMS

REFERENCE TO GOVERNMENT GRANTS

Research for this invention was supported in part by National Institutes of Health Grant AR-38188. The United States government has certain rights in the invention.

FIELD OF THE INVENTION

The present invention relates to the field of methods for detecting genetic diseases and more particularly to the field of methods for detecting genetic diseases linked to abnormalities of collagen genes.

BACKGROUND OF THE INVENTION

The rupture of arterial aneurysms is an important cause of serious disability and death. For example, about 1.3% of the males over 50 years of age in the United Kingdom and in Scandinavia die of rupture of aortic aneurysms. The incidence is lower in women, probably because the earlier development of atherosclerosis in males predisposes the arteries to dilatation and rupture. Cerebral aneurysms are also a frequent cause of morbidity and mortality. The incidence of ruptured cerebral aneurysms is about 4 per 100,000 per year. It is estimated that up to 20% of the general population harbors such cerebral aneurysms. The disease is a devastating one in that as many as 25% of patients who suffer from rupture of a cerebral aneurysm die during the first day and about half succumb in the first three months.

Because of the dire consequences of vascular aneurysm, detection of persons at risk before aneurysms rupture is needed so these persons can be monitored or preventive surgery can be performed.

Type III collagen is a member of the family of fibrillar collagens and accounts for five to twenty per cent of the collagen present in mammals. The Type III procollagen molecule is formed from three identical proα1(III) chains. Each chain contains three separate domains. The N-propeptide domain at one of the chain contains a globular subdomain, a short triple helical subdomain, and finally another short subdomain that forms part of the cleavage site for removal of the N-propeptide. The C-propeptide domain at the other end of the chain is entirely globular. The central, or collagen, domain consists of the α chains. Each of the three α chains is coiled into a left-handed helix, and the three helical chains are twisted around each other into a right-handed superhelix. Each α chain contains about 1,000 amino acid residues, and with the exception of short sequence at the ends of the chains, every third amino acid is glycine. Therefore the molecular formula of an α chain can be represented as (Gly-X-Y), where X and Y denote amino acids other than glycine. The presence of glycine, the smallest amino acid, in every third position is crucial, since the amino acid in this position occupies a restricted space in which the three helical chains come together in the center of a triple helix. Proline and 4-hydroxyproline frequently occupy the X and Y positions, respectively. Assembly of the procollagen molecule involves a large number of post-translational modifications, which require at least eight specific and several non-specific enzymes. In all, over 100 amino acids in each proα chain are modified. In the final conversion of procollagen to collagen, one third of the mass is cleaved from the protein. The Type III procollagen gene (COL3A1) codes for the proα1(III) chains which are then modified to form the mature molecule.

Type III collagen is generally found in association with Type I collagen but is particularly abundant in tissues such as aorta. In contrast, it is absent from bone. The function of Type III collagen has not been fully defined, but its essential role is illustrated by the heritable disorder of connective tissue known as Ehlers-Danlos syndrome type IV in which decreased synthesis or synthesis of structurally abnormal Type III procollagen produces aortic aneurysms and rupture of other hollow organs.

Many variants of osteogenesis imperfecta, the Marfan syndrome, the Ehlers-Danlos syndrome and several related disorders have a genetic component involving defects in collagen genes, specifically, Type I and Type III collagen. In these "collagen diseases" mutations in Type I or Type III collagen genes have been found to cause altered forms of these collagens which in turn result in the physical changes in joints, skin and blood vessels characteristic of each disease. The structure of collagen and heritable "collagen diseases" are reviewed in Prockop and Kivirikko, (1984) New England Journal of Medicine 311: 376-386, prockop, (1985) J. Clin. Invest. 75: 783-787, and Prockop (1986) Hospital Practice February 15, 1986.

Pope et al., (1981) The Lancet May 2, 1981, 973-975 analyzed collagen of patients undergoing surgical treatment for intracranial hemorrhage caused by ruptured cerebral aneurysm and found that seven of the twelve patients with cerebral aneurysm examined were deficient in Type III collagen.

BRIEF DESCRIPTION OF THE DRAWINGS

FIG. 1 shows nucleotide and amino acid sequences of cDNA clones for type III procollagen.

FIG. 2 shows a nucleotide sequence of the 3′ nontranslated region of the human mRNA for type III procollagen.

SUMMARY OF THE INVENTION

The present invention provides methods of screening persons to determine if those persons have an increased likelihood of developing vascular aneurysms. Persons not otherwise known to have a connective tissue disease are screened to detect mutations in the Type III procollagen gene which would indicate an increased likelihood of developing vascular aneurysms. In the methods of the invention, a tissue sample from the mammal is provided and the nucleotide base sequence of at least a portion of DNA coding for proα1(111) derived from the tissue sample is determined. The DNA coding for the proα1(III) chain can be genomic DNA or cDNA prepared from RNA. The nucleotide base sequence of the proα1(III) gene from the mammal is then compared with the nucleotide base sequence of a standard DNA sequence coding for type III procollagen to determine differences in nucleotide bases in corresponding regions of the DNA, whereby a difference in the base sequence of the DNA from the test sample as compared with the standard sequence indicates an increased likelihood of the mammal suffering a vascular aneurysm.

The methods of the invention make it possible to detect mutations in the Type III procollagen gene in persons not otherwise known to have a cônnective tissue disease. The methods of the invention also make it possible to diagnose collagen diseases that are reflected by mutations of the Type III procollagen gene, such as Ehlers-Danlos syndrome type IV, in persons who do not exhibit symptoms of the disease or who have not been diagnosed by physical symptoms of the disease because the symptoms are variable, also indicative of other diseases or too mild for clinical (or physical) diagnosis to be made. While some forms of Ehler-Danlos syndrome type IV can be diagnosed by the presence of physical symptoms alone, the appearance of the disease in the general population may be more variable, with its presence in some persons and families remaining undetected because of the mildness or variability of the physical symptoms.

Applicants have found that mutations in the gene for type III procollagen increase the likelihood of developing vascular aneurysms. Applicants have also discovered that, when present, family members have the mutation in the proα1(III) gene in the same location. Thus, if one family member develops an aneurysm, other family members may be at risk of developing aneurysms. Asymptomatic relatives of the family member can be screened to determine if they have the mutated gene and therefore are prone to develop aneurysms.

Accordingly, the methods of the invention are also useful for detecting genetic familial predisposition to vascular aneurysm. In these methods of the invention, the location of a mutation in the proα1(III) gene of a first family member known or suspected of having vascular aneurysm is determined. The nucleotide sequence of at least the mutated region is then compared to the corresponding region of the proα1(III) gene of a second family member, whereby the presence in the second family member of the mutated region indicates an increased likelihood of vascular aneurysm in the second family member.

If the development of an aneurysm can be detected early, corrective surgery can be effectively carried out so that the section of the blood vessel containing the aneurysm is safely replaced. If, however, the aneurysm develops and ruptures without detection, surgical results are extremely poor. For example, in the case of aortic aneurysms, 85 to 95% of patients die if they are brought to surgery after rupture and bleeding from an aneurysm has occurred. If surgery is performed before the aneurysm begins to bleed, the mortality is only about 5%. Persons found to have a familial predisposition to vascular aneurysm can seek appropriate genetic counseling for family planning.

Although mutations in collagen genes have been demonstrated for diseases such as osteogenesis imperfecta, the Marfan syndrome, the Ehlers-Danlos syndrome and several related disorders, it was heretofore unknown that mutations in the proα1(III) gene are linked to vascular aneurysm in the absence of a connective tissue disease or syndrome. Type III collagen is among the most abundant components of large blood vessels and probably the single most important contributor to the physical strength of blood vessels and their ability to withstand the pressure that is exerted on them by the beating of the heart. Mutations in the proα1(III) gene involving a single base or amino acid substitution may have very subtle effects on the physical properties of procollagen. These mutations might well produce changes in the size or other features of collagen fibrils that make connective tissues less able to withstand the stresses of blood circulation after a number of years. As a result the blood vessels have an increased likelihood of structural failure resulting in aneurysm and ultimately in rupture.

DETAILED DESCRIPTION OF THE INVENTION

The methods of the invention have two stages. In the first stage, a person who has developed an aneurysm, or is suspected of having or developing an aneurysm is tested to determine if he or she has a mutation in the DNA sequence of the proα1(III) gene. The comparison is done by comparing corresponding regions of the DNA sequence of the proα1(III) gene from the person tested with a standard DNA sequence of the proα1(III) gene. The DNA sequence of the proα1(III) gene from the person tested can be genomic DNA or cDNA prepared from RNA derived from a tissue sample obtained from the person. A standard proα1(III) DNA sequence can be obtained by reference to known sequences of the proα1(III) gene, or those set forth herein in FIGS. 1 and 2. A difference in the base sequence of the DNA from the person tested as compared with the standard sequence indicates an increased likelihood of the mammal suffering a vascular aneurysm. For the first family member to be tested, all or a substantial portion of DNA coding for proα1(III) is sequenced and compared to a standard sequence. Sequencing of the first-family member's proα1(III) DNA may be done by conventional DNA sequencing techniques such as in Example 1.

Once the location of the gene mutation is known, it can be looked for in members of the first person's family. For each genetically predisposed individual family member, the mutation of the proα1(III) gene is expected to appear in the same position in the proα1(III) gene. For example, in Family A, the genetic mutation may be at position 25; and for Family B the genetic mutation may be at position 67. Testing the family members can be done by comparing corresponding regions of the family member's proα1(III) gene and the mutation to determine if the mutation is present in the family members in the second stage of the methods of the invention. As used herein, the term family members means persons genetically related to one another in any degree, such as parent-child, siblings, cousins, etc.

In the practice of the methods of the invention, DNA is extracted from a test sample of cells of the family members to be tested by conventional techniques that involve lysis of the cells with sodium dodecyl sulfate (SDS) and digestion of proteins with proteinase K followed by extraction with phenol and chloroform, and ethanol precipitation as described in Maniatis et al., Molecular Cloning: A Laboratory Manual, Cold Spring Harbor Laboratory, Cold Spring Harbor, New York, (1982) pp. 280–281. A sample of cells can be taken from many types of tissues, such as a piece of skin, a sample of blood, or by scraping of the interior of the mouth. Alternatively, mRNA can be extracted from the test sample, and cDNA synthesized with reverse transcriptase and the resulting cDNA used for analysis.

The DNA derived from the cells of the test sample is then analyzed to determine whether or not the gene for type III procollagen contains a mutation. If a mutation is found in the gene for type III procollagen, a rapid test can be devised to test other members of the patients' families to see whether or not they have the same mutation. Family members who have the same mutation can then be followed on a regular basis with non-invasive techniques such as ultrasound or nuclear magnetic resonance to determine whether or not they are developing aortic or cerebral aneurysms. Anyone who is seen to develop an aneurysm can be scheduled for elective surgery to replace the damaged section of the blood vessel before rupture occurs.

Although the methods of the invention have been demonstrated in the first instance in humans, they are expected to be useful in other mammalian species, particularly commercially important species and laboratory animal species used in models of human disease. Type III procollagen sequences for comparison with the DNA sequence of the mammal can be found in the literature, for example in Liau et al., (1985) J. Biol. Chem. 260: 3773-3777 and Wood et al., (,1987) Gene 61: 225-230 for the mouse; and Brandt et al., (1984) Biochem. J. 219: 625-634 for bovines.

EXAMPLE 1

Determination of the Presence Of A Mutation In The proα1(III) Gene

Complementary DNA (cDNA) clones that cover the complete length of the mRNA for human type III procollagen were prepared. To prepare the clones, total RNA (including messenger-RNA) was isolated from cultured human skin fibroblasts by lysis of the cells with Sarcosyl in the presence of guanidinium isothiocyanate and pelleting the RNA through cesium chloride according to the method of Maniatis et. al., supra p 196. Complementary-DNA was synthesized from the poly (A)+ RNA, using a kit purchased by BRL (Bethesda Research Laboratories, Bethesda, Md.) or Pharmacia (Pharmacia - LKB, Piscataway, N.J.) or reverse transcriptase and a primer specific for proα1(III) such as Primer III-21 listed in Table 1. The synthesis of cDNA using reverse transcriptase and primer was performed according to the method of Maniatis et al.,supra pp. 213, 1982. Double-stranded complementary-DNA was synthesized according to the method of Gubler and Hoffman (1983) Gene 25:263-269 as amended by the manufacturers of the cDNA kits. Single-stranded complementary-DNA was synthesized using reverse transcriptase followed by alkaline hydrolysis of the RNA according to Maniatis supra pp. 214-216. The double-or single-stranded cDNA was amplified using a polymerase chain reaction kit (GeneAmp DNA Amplification Reagent Kit, Perkin Elmer Cetus, Norwalk, Conn.) according to instructions provided by the supplier. Primers complementary to different portions of the proα1(III) gene were used in the polymerase chain reaction. The primers used are listed in Table 1.

TABLE I

| | | |
|---|---|---|
| GCCGTCTAGA CTGGTCCTCAGAACTATTCT | XbaI | III-1 |
| CGCAAGCTT GCTCCTGGAAGCCCATTTGC | HindII | III-2 |
| GCCGTCTAGA AGAATAATGGTGCCAAAGGAGAG | XbaI | III-3 |
| CGCAAGCTT GACTTCCAAGACCTCCTCTTTCTC | HindIII | III-4 |
| GCCTCTAGA CCACAAGGATTACAAGGCTTG | XbaI | III-5 |

TABLE I-continued

| | | |
|---|---|---|
| CCCGCAAGCTT AGCTCCTGGTTCCCACTTT | HindIII | III-6 |
| CGGAATTC TTGGGATTGCTGGATCACT | EcoRI | III-13 |
| CGGAATTC ATCAGGACTAATGAGGCTTTC | EcoRI | III-14 |
| CGCAAGCTT TCTCCTCTGTCACCACTCTTT | HindIII | III-19 |
| CGGCGGTACC GGGCAGGGAACAACTTGATG GTGCTACTTT | KpnI | III-20 |
| GGCGAAGCTT CTATGCTACTGTGACAAAAG CAGCCCCATA | HindIII | III-21 |
| CGCAAGCTT GAGTGAAGTCATAATCTC ATCGGTGTTG | HindIII | III-22 |

Several different combinations of primers can be used to generate DNA containing almost all the of Type III procollagen mRNA. A combination of primers III-1, III-2, III-3, III-4, III-5, III-6, III-13, III-14 will provide four overlapping fragments of the proα1(III) mRNA. A combination of primers III-1, III-19 and III-13 and III-14 will provide two overlapping fragments of the proα1(III) mRNA. A combination of III-20 and III-21 will provide the sequences of almost all the proα1(III) mRNA.

To improve the cloning efficiency the primers were designed to include recognition sites for one of the following restriction endonucleases: EcoRI, HindIII, KpnI and XbaI.

After digestion with the appropriate restriction endonuclease(s), the amplified cDNA was ligated into M13mp18 and M13mp19 (Boehringer Mannheim Biochemicals, Indianapolis, Ind.) and digested with the appropriate combinations of restriction endonucleases. The ligated DNA was used to transform *E coli* bacteria and the M13 bacteriophage clones were screened for inserts according to the methods of Messing, J.(1983) Methods in Enzymology 101: 20-78. The sequences of the amplified cDNA fragments were then defined by nucleotide sequencing. Sequencing of the cDNA fragments was done according to the dideoxy nucleotide sequencing method of Sanger et al, (1975). Pro. Natl. Acad. Sci. USA., using the modified T7 DNA polymerase sequence (United States Biochemical Corp., Cleveland, Ohio). Both conventional radioactive sequencing using $^{35}S$ dATP and autoradiography, and sequencing using fluorescently labelled primers and an ABI 370A sequence (Applied Biosystems International, San Francisco, Calif.), were used to determine the sequences. The cDNA sequence determined is shown in FIG. 1 Since the start site for transcription is not known, nucleotides were numbered beginning with the start site for translation. The upper line shows the nucleotide sequence for human type III procollagen. The lower line shows the amino acid sequence for human type III procollagen derived from the cDNA sequence.

The sequences from the first family member (proband) are compared to a standard DNA sequence of the proα1(III) gene such as the DNA sequence in FIG. 1. Portions of the proα1(III) collagen gene sequence have been published previously. The sequence of portions of the proα1(III) collagen gene (from partial cDNA's) can also be found in Liodl et al. (1984) Nucleic Acids Res. 12: 9383–9394; Chu et al. (1985) J. Biol. Chem. 260: 4357–4363; Miskulin et al. (1986) Biochemistry 25: 1408–1413; Mankoo and Dalgleish (1988) Nucleic Acids Res. 16: 2337; and Toman et al. (1988) Nucleic Acids Res. 16: 7201. Changes in the base sequence of the tested family member indicate an increased likelihood of that person developing vascular aneurysm.

This sequence can be used for comparison with the DNA sequence from the person to be tested.

The DNA sequence shown in FIG. 2 is the nucleotide sequence a portion of the 3' non-translated region of the human mRNA for type III procollagen. This sequence was previously published in Mankoo & Dalgleish, 1988. Symbols: underlined bases, differences in nucleotide sequence from previously published sequence for same region (Mankoo & Dalgleish, 1988); asterisks, insertions of additional bases not found in previously published sequences; vertical arrows, sites at which additional nucleotides were observed in previous cDNA clones; rectangular boxes, sequences of AATAAA- that are probably signals for polyadenylation. Mutations in the untranslated portions or "intervening sequences" may be important to the final structure of Type III collagen because a mutation in a region close to a splicing site may prevent normal splicing and result in an abnormal Type III procollagen molecule.

EXAMPLE 2

Isolation and characterization of genomic clones covering exons 17 through 45 and part of exon 16 of the human proα1(III) gene Genomic clones for the human type III procollagen gene, i.e., clones of DNA that contain not only the coding sequences that determine the amino acid sequence of the protein and are contained in complementary-DNA, but also clones containing additional DNA sequences on either side of the gene ("flanking sequences") and within the gene ("intervening sequences" or "introns") were developed by the following method.

DNA was isolated from cultured human skin fibroblasts by a method involving lysis with SDS, digestion with Proteinase K, extraction with phenol and chloroform, and ethanol precipitation. Isolated DNA was digested to completion with the restriction endonuclease BamHI. The size fraction enriched for 13000 bp fragments was isolated by centrifugation through a 10–40 percent sucrose gradient according to the methods of Maniatis supra pp.284–285. Previously, it was reported by Chu et al., supra that a 13000 bp BamHI fragment was present in the type III procollagen gene. The DNA enriched for 13000 bp fragments was ligated into the bacteriophage lambda vectors EMBL (Promega, Madison, Wis.) and Dash (Stratagene). The ligated DNA and bacteriophage lambda vector was packaged using the packaging extract Packagene (Promega, Madison, Wis.). The bacteriophage was used to infect a host strain of *E. coli* and the plaques were screened for clones containing type III procollagen inserts using a standard plaque lift assay according to Maniatis supra pp.320–321 and a radioactively labelled fragment of the type III procollagen gene as a probe. Positive plaques were purified to homogeneity and restriction endonuclease fragments were subcloned into the filamentous bacteriophage M13mp18 and M13mp19 for sequence analysis. Approximately 8000 bp of the insert was sequenced. The sequence revealed that the 13000 bp fragment contained part of exon 16 as well as exons 17 through 45 as well as introns 16 through 44 and part of intron 45. The exon derived sequences were identical with those of the cDNA for the corresponding regions.

EXAMPLE 3

Testing of other family members for mutation in the proα1(III) collagen gene Once the location of the mutation in the Type III procollagen gene in known, other family members can be tested to determine if they also have the mutation in their Type III procollagen genes, thus making them more likely to develop vascular aneurysms. Testing other family members can readily be done by probing the family member's DNA with a nucleotide probe having a base sequence complementary to the mutation in the first family member. The DNA from the other family members can be genomic DNA or cDNA synthesized by conventional techniques using reverse transcriptase and mRNA template.

A preferred test format is a nucleic acid hybridization assay such as dot or slot blot assays or Southern transfer of DNA fragments after separation on agarose gel. Other methods such as restriction endonuclease digestion of amplified DNA followed by agarose gel electrophoresis and visualization of the DNA by Ethidium Bromide, if the mutation has created or destroyed a restriction endonuclease recognition site may also be suitable for detecting the mutation in family members.

A DNA probe having a sequence which includes the mutation in the first family member's Type III procollagen gene is synthesized using standard techniques. The probe is preferably approximately 15 to approximately 30 nucleotides in length, more preferably approximately 18 nucleotides in length. The actual nucleotide sequence of the probe will depend on the location of the mutation in the Type III collagen gene. The probe will contain the mutation with normal flanking nucleotides upstream and downstream of the mutation and is synthesized in the sense direction of the gene. The nucleotide sequence of the probe is complementary to the sequence of the corresponding DNA it is designed to detect.

A second probe having the standard or normal base sequence for the corresponding region is also synthesized using standard techniques. The second probe is preferably approximately 15 to approximately 30 nucleotides in length, more preferably approximately 18 nucleotides in length and the same length as the first probe. The second probe is also complementary to the corresponding DNA sequence it is designed to detect.

Both probes may then be labeled with a detectable label, preferably a radiolabel such as $^{32}P$. The probes may be labeled with $^{32}P$ using standard methods, such as ATP labeled with $^{32}P$ on the 8 (gamma) position and $T_4$ Polynucleotide Kinase according to the method of Maniatis et al., supra. Non-radiolabeled probes that contain biotinylated nucleotides introduced during the oligonucleotide synthesis may also be used. Detection of the biotinylated nucleotides may be accomplished by strepavidin and antibody-linked enzymes that generate a color reaction, such as that in the Genius system (Boehringer Mannheim Biochemicals, Indianapolis, Ind.). Other types of detectable labels may also be used.

If a hybridization assay indicates the mutation in the proα1(III) gene is present in the DNA of the family member, the diagnosis can be verified by sequencing the region of the gene suspected of containing the mutation using standard DNA sequencing techniques.

The DNA of the family member can be tested with or without prior amplification of the portion of the gene suspected of containing the mutation. If the family member's DNA is to be amplified prior to hybridization, primers for the polymerase chain reaction can be selected and synthesized using conventional techniques from base sequences flanking the region of the mutation, care being taken that there is no overlap of the sequence of the probe and the primers. The particular sequence of the primers will depend on the location of the mutation of the Type III procollagen gene in the first family member. Reference is made to the sequence of the Type III procollagen gene shown herein for the sequence of the primer. For example, if the mutation in the proα1(III) collagen gene is at base 100, a probe containing the mutated base could be selected to span bases 90 to 108. Primers would then be selected to span non-overlapping bases outside this area. The sequences of the primers would be selected to correspond to the base sequence of the proα1(III) gene in the selected areas. The particular sequence can be determined from the sequence shown herein. Primers are preferably from approximately 25 to approximately 50 nucleotides in length, more preferably about 35 to forty nucleotides in length. The polymerase chain reaction is performed according to U.S. Pat. Nos. 4,683,195 or 4,683,202 or commercially available kits (Cetus Corporation, Emeryville, Calif.).

EXAMPLE 4

Familial history of vascular aneurysms as a result of mutation in the Type III procollagen gene Skin fibroblasts were examined from a 38-year old woman with a strong family history of aneurysms that ruptured and produced death. The woman was an officer in the Air Force and physically fit. She had mild hyper-extensibility of joints, but no other evidence of connective tissue disease. Her mother and two of her mother's siblings died of ruptured aortic aneurysms. In addition, one first cousin died at the age of 13 of a ruptured abdominal aneurysm and another died suddenly at the age of 21 of undetermined causes. One direct blood relative died of a cerebral vascular accident that may have been caused by a ruptured cerebral aneurysm.

DNA from the proband was analyzed according to the methods described herein. Briefly, messenger-RNA from the cultured skin fibroblasts of the proband was used to prepare complementary-DNA. The complementary-DNA were then analyzed with a series of primers based on the normal structure of type III procollagen complementary DNA. Primers were used in a polymerase chain reaction to generate a series of DNA fragments that included most of the coding sequences of the gene. The DNA fragments obtained from the polymerase chain reaction were then analyzed in detail for their nucleotide sequence. The results indicated that the patient had a mutation in one of her two alleles for type III procollagen that converted the codon for glycine 619 of the α1(III) chain to a codon for arginine. The mutation was a single-base mutation. Extensive analysis of DNA fragments containing the remaining coding sequences of the gene showed no evidence of a second mutation. Based on these observations, the substitution of arginine for glycine is very likely to seriously disrupt the normal triplehelical structure of the type III procollagen molecule. The disruption of the structure probably makes the type III procollagen produced from the mutated gene a much weaker fibrous protein and predisposes large blood vessels to rupture. The results strongly suggest that the mutation in the proband's type III procollagen gene was the cause of the aneurysms and death that occurred in her immediate blood relatives.

Subsequent history and examinations of this patient revealed physical symptoms indicating that she most likely has a mild form of Ehlers-Danlos syndrome type IV. The methods of the invention made it possible to diagnose this patient, since she did not upon first examination show definite symptoms of Ehler-Danlos syndrome type IV.

We claim:

1. A method of detecting a genetic predisposition for vascular aneurysm in a person not otherwise known to have a connective tissue disease, comprising identifying a person suspected of having a genetic predispositon for vascular aneurysm;

providing a tissue sample from said person;

determining the nucleotide base sequence of at least a portion of DNA coding for proα1(III) derived from said tissue sample; and determining at least one difference in nucleotide base sequence of corresponding regions of said tissue sample DNA and a standard DNA sequence coding for type III procollagen, whereby a difference in the base sequence of the DNA from the test sample as compared with the standard sequence indicates an increased likelihood of said person suffering a vascular aneurysm.

2. A method of detecting genetic familial predisposition to vascular aneurysm in patients not otherwise known to have a connective tissue disease, comprising the steps (a) determining the location of a mutation in the proα1(III) gene of a first family member known or suspected of having vascular aneurysm; and (b) determining whether the proα1(III) gene of a second family member of the mutated region indicates an increased likelihood of vascular aneurysm in the second family member.

3. The method of claim 2 wherein said determining step comprises (a) providing a tissue sample from said first family member;

(b) amplifying at least a portion of DNA coding for type III procollagen in said tissue sample;

(c) comparing the nucleotide base sequence of said amplified DNA with the nucleotide base sequence of a standard DNA sequence coding for type III procollagen to determine at least one difference in nucleotide bases in corresponding regions of the DNA, whereby a difference in the base sequence of the DNA from the test sample as compared with the standard sequence indicates an increased likelihood of said first family member suffering a vascular aneurysm.

4. The method of claim 1 wherein the difference in base sequence of the DNA from the test sample results in the DNA sequence coding for a different amino acid.

* * * * *